(12) United States Patent
Siedler et al.

(10) Patent No.: US 9,138,326 B2
(45) Date of Patent: Sep. 22, 2015

(54) JOINT IMPLANT

(75) Inventors: Uwe Siedler, Alzenau (DE); Frank Bleistein, Alzenau (DE)

(73) Assignee: Taurus GmbH & Co. KG, Alzenau (DE)

( * ) Notice: Subject to any disclaimer, the term of this patent is extended or adjusted under 35 U.S.C. 154(b) by 188 days.

(21) Appl. No.: 13/543,043

(22) Filed: Jul. 6, 2012

(65) Prior Publication Data

US 2013/0110244 A1    May 2, 2013

(30) Foreign Application Priority Data

Jul. 8, 2011    (DE) ............... 20 2011 103 010 U

(51) Int. Cl.
*A61F 2/44* (2006.01)
*A61F 2/30* (2006.01)

(52) U.S. Cl.
CPC ............. *A61F 2/442* (2013.01); *A61F 2/4425* (2013.01); *A61F 2002/3063* (2013.01); *A61F 2002/3093* (2013.01); *A61F 2002/30375* (2013.01); *A61F 2002/30387* (2013.01); *A61F 2002/30426* (2013.01); *A61F 2002/30434* (2013.01); *A61F 2002/30448* (2013.01); *A61F 2002/30451* (2013.01); *A61F 2002/30504* (2013.01); *A61F 2002/30604* (2013.01); *A61F 2002/30632* (2013.01); *A61F 2002/30841* (2013.01); *A61F 2002/30932* (2013.01); *A61F 2002/30935* (2013.01)

(58) Field of Classification Search
USPC ............... 623/17.11–17.16; 403/348, 329
See application file for complete search history.

(56) References Cited

U.S. PATENT DOCUMENTS

| 6,966,818 | B1 | 11/2005 | Carlson, III |
| 7,695,516 | B2 * | 4/2010 | Zeegers ............... 623/17.14 |
| 2002/0172550 | A1 * | 11/2002 | Uhler et al. ............... 403/348 |
| 2004/0225364 | A1 * | 11/2004 | Richelsoph et al. ....... 623/17.13 |
| 2006/0142862 | A1 | 6/2006 | Diaz et al. |
| 2006/0241770 | A1 * | 10/2006 | Rhoda et al. ............ 623/17.15 |
| 2007/0067037 | A1 | 3/2007 | Studer |
| 2010/0292794 | A1 | 11/2010 | Metz-Stavenhagen |
| 2012/0150298 | A1 * | 6/2012 | Bennett et al. ............ 623/17.11 |

FOREIGN PATENT DOCUMENTS

| AU | 2009295391 | * | 4/2010 |
| DE | 20307876 U1 | | 9/2004 |
| DE | 202008012749 U1 | | 2/2010 |
| WO | 2005/094732 A1 | | 10/2005 |
| WO | 2007/092144 A2 | | 8/2007 |
| WO | WO/2010/034287 | * | 4/2010 |

OTHER PUBLICATIONS

EP Search Report issued Jan. 21, 2013 in EP Application No. 12175102.8.

* cited by examiner

*Primary Examiner* — Jan Christopher Merene
(74) *Attorney, Agent, or Firm* — Panitch Schwarze Belisario & Nadel LLP

(57) ABSTRACT

A joint implant includes an upper and a lower implant part which are connected to each other, and a longitudinal axis of the implant. The implant parts each include a joint part having a joint region and an abutment part that can be abutted against the respective bone. The joint part and the abutment part are detachably connected to each other. The two joint parts each include a joint region and cooperate with each other, thus forming the articulated connection, or with an intermediate element having opposite upper and lower sides as abutment surfaces, thus forming two sub-joint. A connecting device interconnects the upper and lower implant part so as to form a coherent assembly and that can change its position relative to the upper and/or lower joint part.

24 Claims, 4 Drawing Sheets

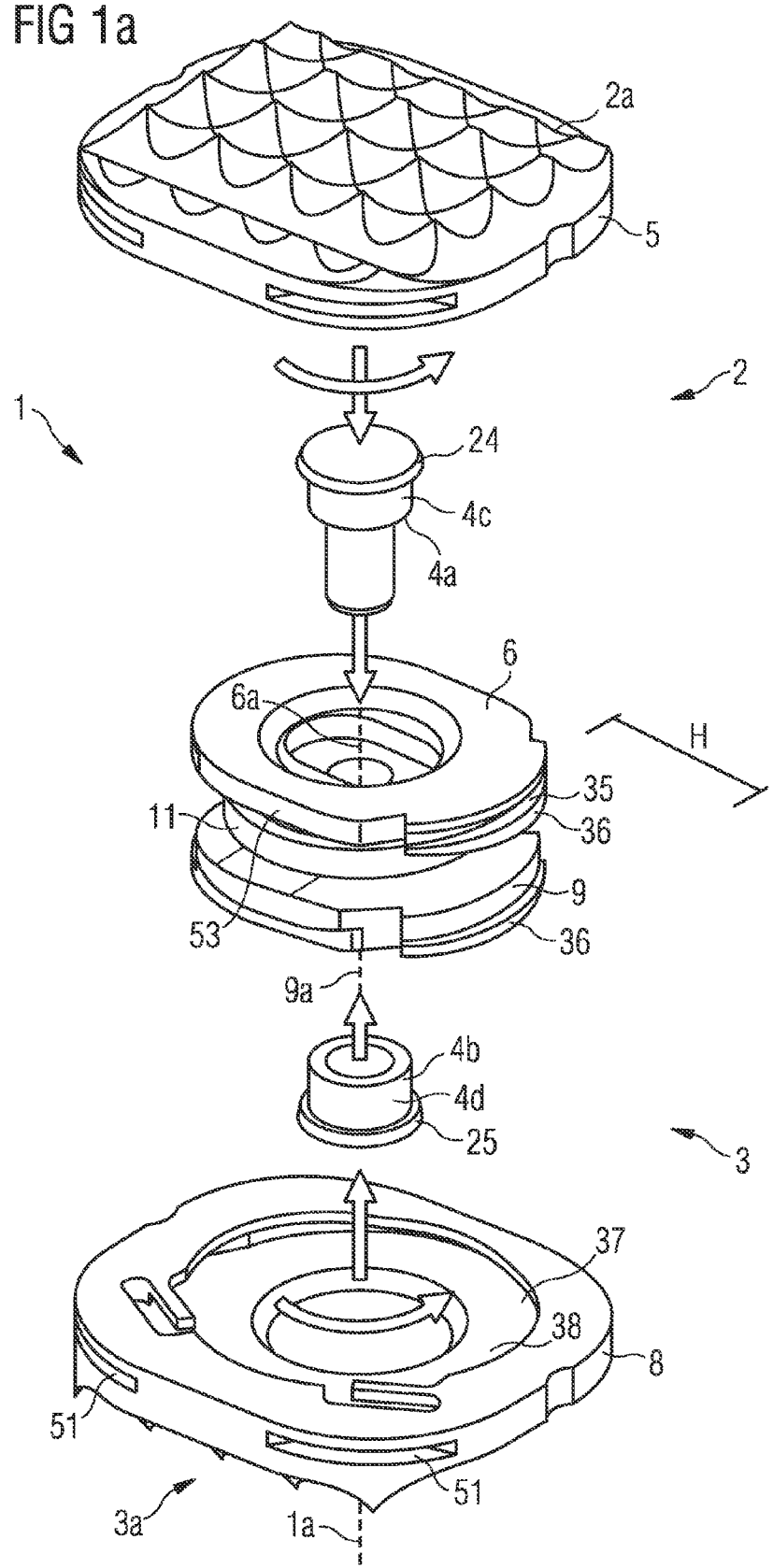

FIG 4
FIG 4a
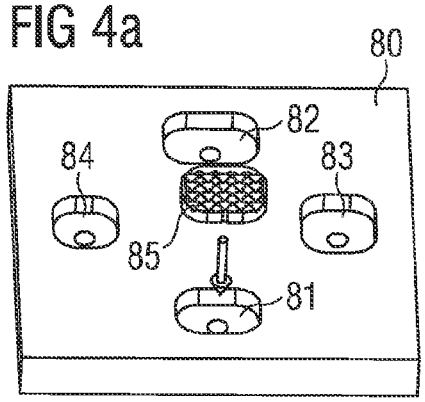
FIG 4b
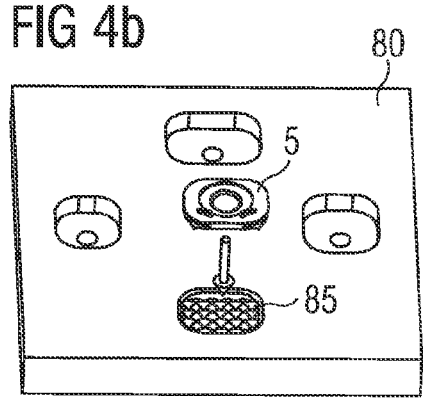
FIG 4c
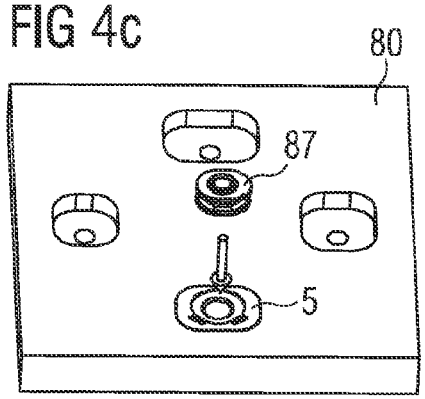
FIG 4d
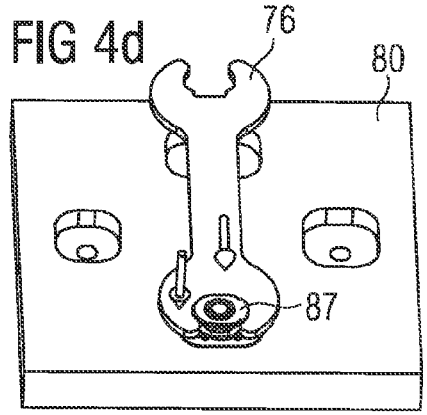
FIG 4e
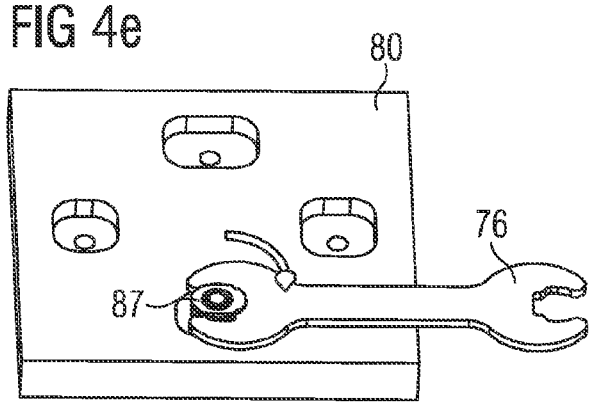
FIG 4f
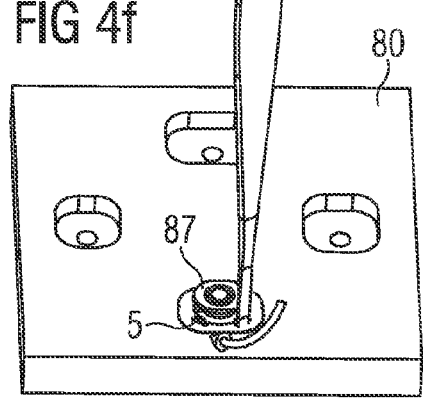

JOINT IMPLANT

BACKGROUND OF THE INVENTION

The present invention relates generally to a joint implant.

Such joint implants are used for instance as intervertebral disk prostheses for interconnecting adjacent vertebrae in an articulated manner. The implant can have one or more joint regions that afford an articulated motion of the respective parts of the implant to each other and independently from each other, for instance pivoting or tilting motions against each other. The implant can thus have two different joint regions, each of which performs pivoting or tilting motions about a pivoting or tilting axis that is arranged in a plane transverse to the longitudinal axis of the implant, the two axes being arranged at an angle to each other.

For adapting the implant to the respective anatomical conditions while affording easy handling of the implant preparatory to its implantation and also during the implantation, it turned out to be advantageous for the upper and/or lower implant part to include a joint part on the one side, the joint part providing the joint region of the respective implant part so that the two adjacent joint regions of the two implant parts or the respective joint region of the implant plant together with the abutment surface of the intermediate part form an articulated connection. Thus, the implant can be easily configured in such a manner that it suits different bones with differently large implant abutment surfaces and/or different distances of the bone connecting regions to each other, namely by selecting suitable joint parts. The joint can be adapted in an easy manner to patients with differently sized vertebrae and/or to patients with different weights.

Furthermore, on the one side the various implant parts are required to be fixed to each other for allowing the implant to be implanted as a pre-mounted assembly, which makes the implantation considerably easier. On the other side, the connection between the individual implant parts is required to resist high mechanical loads over a longest possible period of time because the implant is subject to high forces that are exerted while the respective patient moves and also because the implant parts must perform complex combined motions relative to each other, e.g. pivoting motions, torsional motions, combined pivoting and torsional motions or the like, as a result of complex motions of the patient. The connection of the implant parts must be durable even in the case of such complex motions and under high forces.

Further, such an implant or its individual component parts must be easy sterilizing.

An implant of the kind which has been described is known from DE 20 2008 012 749, in which the upper and the lower implant part each consist of a joint part and an abutment part that can be abutted on the respective bone, the parts being connected to each other to form a coherent assembly by means of a connecting element. To this end, the joint part is moved into a laterally open recess, with the insertion direction lying in a plane parallel to the two main planes of the two components, and the joint part is then fixed to the abutment part in such a manner that it is secured against sliding by means of a snap connection. While such an implant has delivered satisfying performance on various occasions, the disadvantage of that implant is that the implanted implant parts and abutment parts may become detached from each other during complex motions of a patient, which involves the risk of injury, particularly spinal injuries. Solving this problem by making the snap connection between the joint parts and the abutment parts more robust has turned out to be infeasible because this also impedes the mounting of the implant.

Accordingly, it is an objective of the present invention to provide an implant of the above-described kind which has a long service life and can be easily mounted also under the influence of high forces and complex motion profiles. It also is an objective of the present invention to provide a device which simplifies mounting of the implant. The present invention accomplishes the above objectives.

BRIEF SUMMARY OF THE INVENTION

According to a preferred embodiment of the invention, the joint part and the abutment part of at least one or of both implant parts include fixing devices which are designed as form-closure devices which cooperate or are caused to cooperate with each other while twisting the joint part and the abutment part. By the fact that the form-closure devices of the respective joint part and abutment part can be fixed to each other under twisting, the implanted implant is secured to the greatest possible extent against a separation of the joint part from the abutment part under complex motions of the patient. In particular, a separation of the joint part and the abutment part in a direction vertical to the longitudinal axis of the implant or to the longitudinal axis of the vertebral column is virtually prevented. The seats of one of the joint part and abutment part for receiving the other one of the two parts (e.g. a seat provided in the abutment part for receiving the fixing region of the joint part) can thus be fully or almost fully closed in relation to a circumference, the circumference lying in the main plane of the implant part and hence being arranged vertically to the longitudinal axis of the implant or to the longitudinal axis of the vertebral column. A spacing of the joint part and the abutment part to each other in any direction in the main plane of the implant part is thus excluded, and numerous tests that have been carried out within the scope of the present invention have shown that this construction of the implant effectively prevents a separation of the joint part and the abutment part also under high complex loads (complex in respect of the motion type and motion direction of the change of position of the parts of the implant relative to each other). The form-closure devices which cooperate under a twisting motion of the joint part and the abutment part against each other additionally provide a safeguarding device against twisting of the two parts against each other, thus counteracting a separation of the two parts from each other. Thus, the form-closure devices are effective at the same time as a safeguarding device against a twisting motion of the joint part and the abutment part against each other. On the other hand, as the two implant parts are twistable against each other and particularly against the intermediate element—preferably independently of each other with respect to the intermediate element—the resistance to a twisting motion of the implant parts against each other (particularly the frictional resistance) is smaller in the use of the implant installed in the patient than the resistance provided by the form-closure devices to a twisting motion of the joint part and the abutment part against each other. The implant is constructed in such a way that a twisting motion of both implant parts against each other is freely possible through an angle that corresponds to the maximum twist position of two adjacent vertebrae of a vertebral column, particularly a vertebral column of a mammal and especially of a human being. In particular, the implant is constructed in such a manner that a twisting motion of the upper and lower implant parts relative to the intermediate part (in relation to the total angle of twist of the two implant parts relative to the intermediate part) is equal or greater than the anatomical twist angle of adjacent vertebrae of a vertebral column of a mammal and especially of a human being. Particularly preferably, a free twisting motion of the upper and/or lower implant parts against each other is possible at an angle of ≥20-40° or preferably ≥60-120° or ≥180-240° or even more preferably by about 360°. Furthermore, preferably in combination therewith, a free twisting motion of the upper and/or lower implant parts against the intermediate part is possible at an angle of ≥60-120° or ≥180-240° or even more preferably by about 360°. On the one side this enables the implant to be inserted as flexibly as possible in different vertebrae or joints while guaranteeing on the other side that at the given free twistability of the implant parts against each other or against the intermediate part the angular range of the free twistability is so wide that the form-closure devices between the joint part and the abutment part are not loaded, at least not loaded by a force that is considerably higher than the force to be overcome at the free twistability of the upper and lower implant parts to each other (where applicable with an intermediate element arranged there between). Where applicable, the force for overcoming the form closure between the joint part and the abutment part is ≥ than 2 to 5 times or ≥ than 10 to 20 times or particularly preferably ≥ than 50 to 100 times the force of the free twistability of the upper and/or lower Implant parts to each other. Particularly preferably, in the twisting motion of the joint part and abutment part to each the form-closure devices can be overcome only upon destruction thereof, unless the same are disengaged by a separate operation.

Particularly preferably, the upper and/or lower joint part has a back with a back line, preferably a straight back line, and the joint part can roll off with the back against the abutment surface of the intermediate element. The back may have a curved cross section, preferably curved in a circular arc shape. Laterally of the back, on one or both sides thereof, abutment surfaces can be provided that can be applied flat against the surfaces of the intermediate element while restricting the roll-off motion of the joint part against the intermediate element. The surface of the intermediate element which forms the abutment surface for the back of the joint part can be plane, which preferably applies for both abutment areas of the intermediate element against the respective back of the two joint parts, preferably with a plane-parallel orientation of both abutment surfaces. Particularly preferably, the intermediate element is formed as a disc, particularly as a disc having two plane-parallel surfaces that are turned towards the respective joint parts.

This altogether provides an implant which is very securely mounted and has a long service life even if subject to complex motions of the joint parts to each other and that can be easily sterilized as a result of its large seats.

Preferably, the two implant parts can be moved against each other in a transverse and preferably vertical direction to the longitudinal axis of the implant. To this end, the joint region of at least one or both implant parts can be provided with a long hole for the passage of the connecting device that connects the upper and the lower implant part to form a coherent assembly. The connecting device can then be moved inside the long hole transversely to the longitudinal axis of the implant. The longitudinal sidewalls of the long hole can extend parallel to each other and in a straight fashion so that the long hole exhibits a constant width. Preferably, the long hole extends in a straight fashion. Where necessary, the long hole can also have differently wide sections in the longitudinal direction, wherein the section with the largest width is preferably arranged in the center of the long hole and wherein the long hole tapers towards one or both ends thereof. The long hole may or may not restrict a displacement of the connecting device in the longitudinal direction of the long hole with respect to changes of the position of the joint parts to each other, which changes of position are anatomically still permitted in the movement of a respective patient (so that at least one or both ends of the long hole serve as a stopper for the connecting element for preferably none of the two ends of the long hole serves as a stopper for the connecting element in the). Transversely to its longitudinal direction, the long hole preferably has a width such that it serves as a lateral guide for the connecting element in the movement of the connecting element, but preferably as a guide with a lateral play so that the lateral width of the long hole is greater than the diameter of the passage area of the connecting device. The construction of the implant according to that preferred embodiment of the present invention turned out to be particularly beneficial because due to the permitted displacement of the two implant parts against each other in the implant main plane during a patient's movement, transverse forces can be exerted on the implant parts which can be completely absorbed in the implant according to the invention, since the joining direction of the joint part and the abutment part in which the two component parts can be joined to each other prior to performing the twisting motion for causing the form-closure means to cooperate, may lie at an angle to the implant main plane, for example at an angle of ≥±30–±60°, particularly preferably vertically to the implant main plane. This permits particularly high transverse forces to be absorbed by the joint connection.

Particularly preferably, the fixing devices for fixing the joint part and the abutment part to one another includes at least on one or both implant parts a male and a female form-closure device, which cooperate for fixing. The male form-closure device comprises a pin with e.g. a non-round cross section and with holding areas that preferably radially protrude from the pin circumference. The female form-closure device comprises a preferably non-round seat with undercuts, which seat is formed for receiving the male form-closure device in a preferably congruent manner. The form-closure devices can be joined in a join position in which the male fixing device is arranged in the seat. By twisting the form-closure devices against each other the same can be moved to a fixing position for fixing the joint part and abutment part to one another. The arrangement of the at least one holding area in the undercut provides for secure fixing of the joint part and the abutment part to one another. At the insertion of the holding area in the undercut, the holding area can override an ascending slope in the form of a thread lead, to become fixed in its desired position in the axial direction of the pin between the regions forming the undercut. But it is also possible for the holding area to be accurately fitted in the undercut so that the holding area is arranged in the undercut without axial play. The form-closure devices can thus cooperate in the manner of a bayonet joint.

Particularly preferably, anti-twist safeguarding devices are provided which lock the joint and abutment parts that are fixed to one another in their desired position in a relatively non-twistable manner. The anti-twist safeguarding devices can be provided on one of the components, namely the joint part and the abutment part, preferably on the joint part and particularly preferably on the radially protruding areas of the pin. On the seat of the respective other component, namely preferably the abutment part, which seats corresponds with the pin, the anti-twist safeguarding device can be provided on the seat, preferably in a region that includes the undercut for the axial fixing of the holding areas of the respective other component. By that anti-twist safeguarding device the joint part and the abutment part are securely fixed to one another even in the case of complex motions of the joint parts of the implant to each other.

Particularly preferably the twist lock means are designed in a manner such as to secure the joint part and the abutment part against twisting relative to each other in both twisting directions, i.e. during the right hand rotation and also during the left hand rotation. Particularly preferably, the implant part respectively includes at least two anti-twist safeguarding devices to lock the joint part and the abutment part against twisting in opposite twisting directions. This permits particularly high torsional moments to be absorbed by the twist lock means. Furthermore, the anti-twist safeguarding devices can be released and/or operated independently, thus enabling the joint part and the abutment part to be twisted against each other in one twisting direction and to be locked against twisting in the opposite direction, which can be advantageous for demounting the implant part. A particularly advantageous preferred embodiment of the present invention provides for the anti-twist safeguarding devices to be designed as pivot or locking means that engage in a corresponding recess or retaining area of the corresponding component to lock the same against twisting.

A preferred embodiment of the invention further includes a mounting plate for mounting an implant according to the present invention. The mounting plate at least includes one recess for receiving an abutment part. The seat is preferably adapted to the contour of the abutment part in such a manner that the abutment part is received in the seat of the mounting plate in a manner secured against twisting. That permits simple mounting of the implant parts or of the implant as a whole, wherein the abutment part that includes the seat for the fixing devices of the joint part is exposed and can be easily supported by the mounting plate when the components are twisted to each other. The mounting plate can comprise several seats so that all the component parts of the implant can be mutually separately supported on the mounting plate. That enables the mounting plate to be loaded with several or preferably all single component parts of the implant, wherein the component parts are adapted to a respective patient's anatomical conditions so that the implant parts can be examined for their accurate design and/or appropriate matching with regard to the patient's anatomical conditions.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1a is an exploded perspective view of an implant according to a preferred embodiment of the present invention;

FIGS. 4a-4f are perspective views of a mounting plate carrying parts of the implant during sub-assembly of the implant.

DETAILED DESCRIPTION OF THE INVENTION

Figure 1B:
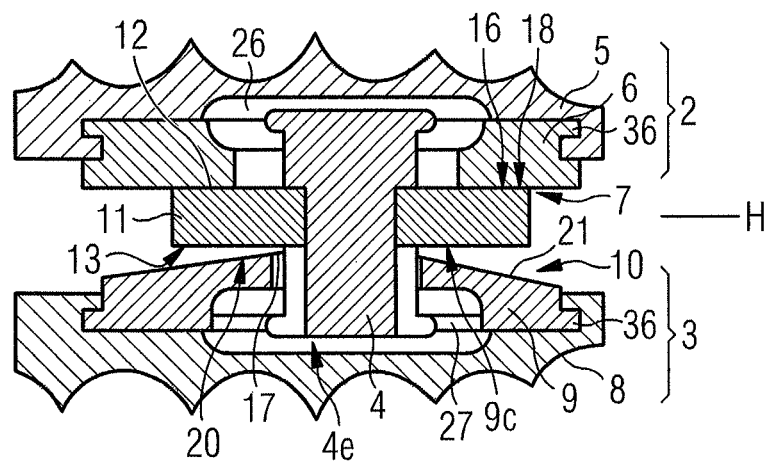
FIG. 1b is a cross-sectional elevational view thereof, wherein the implant is in a mounted state.

Certain terminology is used in the following description for convenience only and is not limiting. The words "right," "left," "lower," "upper" and "top" designate directions in the drawings to which reference is made. The word "outwardly" refers to a direction away from a geometric center of the device, and designated parts thereof, in accordance with the present invention. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals indicate like elements throughout the several views, FIGS. 1a-3c show one preferred embodiment of a joint implant 1 according to the present invention preferably including an upper and a lower implant part 2, 3 and an implant longitudinal axis 1a. The upper implant part 2 and the lower implant part 3 can be applied with the respective upper side 2a and lower side 3a against the contact areas of bones, particularly against the base plates of adjacent vertebral bodies, for interconnecting the same in an articulated manner. The abutment part has a continuous closed surface facing the associated bone. The upper implant part 2 and the lower implant part 3 can be applied and supported with their upper side and lower side respectively against bones that are to be connected to each other in an articulated manner.

Further, a connecting device 4 is preferably provided which interconnects the two implant parts 2, 3 in such a manner that they form a coherent assembly while permitting an articulated motion. The upper implant part 2 preferably includes of an abutment part 5 having the upper side 2a of the implant part which can be applied against the bone, and of a preferably separate joint part 6 that is fixed to the abutment part 5 and provides the joint region 7 of the upper implant part. The lower implant part 3 correspondingly includes an abutment part 8 providing the lower side 3a as well as a preferably separate joint part 9 that is fixed to the abutment part 8 and provides the joint region 10 of the lower implant part. The joint part 6 and the abutment part 8 of the respective implant part are detachably connected to each other by fixing devices and the respective connection of the implant and joint parts to each other can also be dissolved. The two abutment parts and the two joint parts of the exemplary implant are illustrated identically in construction in FIG. 1, but twisted relative to each other by 90°. The two abutment parts and the two joint parts of the implant can be differently configured separately from each other, particularly the joint regions of the two joint parts can be different, e.g. with different curvatures and/or widths of the backs and/or different inclinations of the preferably plane areas joining the backs laterally, which areas restrict the roll-off movement by abutment against the intermediate element. These designs according to the preferred embodiment can generally apply for only one of the two implant parts of the implant of the invention, e.g. for the upper or for the lower implant part, but particularly they apply for both implant parts of the implant.

The two joint regions 7, 10 of the upper and lower implant parts can directly cooperate, where necessary, so as to form an articulated connection. However, according to the preferred embodiment, an intermediate element 11 is provided between the two implant parts 2, 3 which includes an upper and a lower side 12, 13 respectively facing the upper and the lower abutment part 5, 8 and each cooperating with the joint surfaces 16, 17 of the joint parts 6, 9 while being applied against the same in order to form two joint parts of the implant. The two joint regions 7, 10 or the two sub joints can be operated or moved separately from each other. The connecting device 4 preferably inseparably connects the upper and the lower implant parts 2, 3 so as to form a coherent assembly. The connecting device 4 can change its position with respect to the upper and/or lower joint part 6, 9, preferably at least with respect to one of the joint parts. The connecting device can be twisted relative to the upper and/or lower joint part about the longitudinal axis 6a, 9a thereof and can preferably be slightly displaced axially against the same at least in individual articulated positions of the implant (preferably also in the neutral position). The connecting part can be displaceable in its position relative to the intermediate part independently or in combination therewith, for example, it can be twistable relative thereto and/or displaceable in the main plane of the implant, but preferably the connecting device 4 is fixed in its position relative to the intermediate part 11. The connecting device 4 can be displaceable with respect to the joint parts 6, 9 in the implant main plane H (which is perpendicular to the axis 1a) in at least one or preferably in precisely one direction, which can be predefined by a long hole 6b, 9b of the respective joint part.

The upper and/or lower sides 12, 13 of the intermediate element 11, preferably both sides, are plane in the present case and are preferably arranged so as to be plane-parallel to each other. While forming sub-joints, the joint surfaces 16, 17 can each change their position with respect to the surfaces 12, 13 of the intermediate element 11, particularly in a roll-off motion (possibly also in a pivoting or tilting motion, which is clearly less practicable). The axis about which the respective roll-off motion is performed can include an angle of 90° to the longitudinal axis of the implant. For performing the roll-off motion, the joint surfaces 16, 17 are each provided with a centrally arched, preferably circular arc-shaped roll-off area in the form of a back, which respectively protrudes towards the intermediate element 11. The term "roll-off motion" means that the line of the joint regions of the joint part and hence the ridge of the back which is applied against the intermediate element in the neutral position of the implant lifts off the contact surface of the intermediate element during the roll-off motion and is thus separated from the intermediate element (differently from a ball joint design) by a gap 9c (which is also the case with the joint part 6 here hidden by the joint part). This fact is important for an anatomically advantageous construction of the implant. The regions enabling the roll-off motion, here the joint regions 7, 10 formed as roll-off areas, are respectively joined by preferably plane abutment areas 20, 21 that are provided on the upper (not illustrated) and lower joint parts and which preferably afford a flat contact with the upper and lower side of the intermediate element while at the same time restricting the articulated motion. In the neutral position of the respective upper and lower implant part, i.e. with the abutment surfaces arranged perpendicularly to the longitudinal axis of the implant, the abutment areas 20, 21 of these parts can respectively have the same or a different inclination to the longitudinal axis 1a of the implant, which can also coincide with the longitudinal axis of the connecting device 4. The upper and the lower joint part can be different with regard to the design of the joint areas, for example with regard to the radius of crown or curvature of the central roll-off areas and/or the inclination of the laterally adjoining abutment areas 20, 21 to the longitudinal axis of the implant. The design complies with the anatomical requirements. The upper and the lower abutment part 5, 8 can normally be equally designed, independently of the embodiment. The individual component parts, i.e. the upper and the lower abutment part 5, 8, the upper and the lower joint part 6, 9 and the intermediate element 11 can be formed as substantially plate-like components. The upper and the lower implant part 2, 3 are designed in such a manner that they are twistable about the longitudinal axis 1a of the implant against each other and against the intermediate element.

Figure 2:
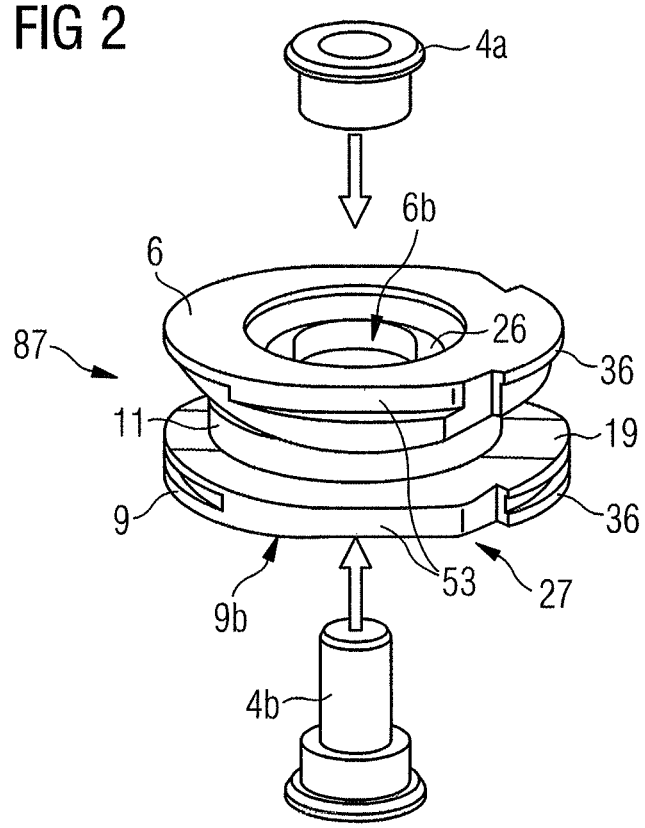
FIG. 2 is an exploded view of an assembly of two implant parts including connecting devices of the implant shown in FIG. 1.
Figure 3A:
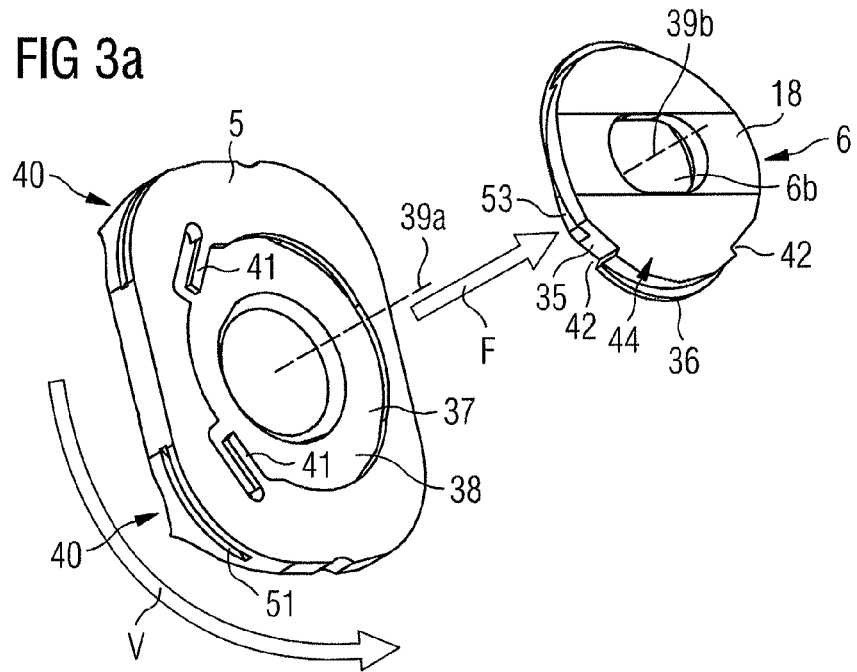
FIG. 3a is an exploded view of an arrangement of an abutment part and a joint part.
Figure 3B:
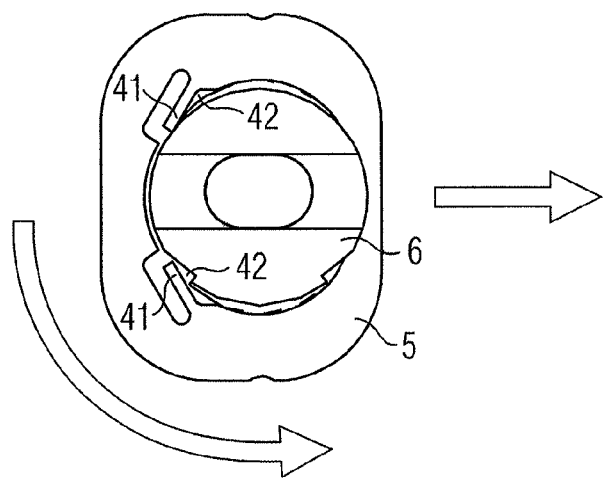
FIG. 3b is a top view thereof in a joined state.

In the articulated motion, a kind of "slippage" of the roll-off area over the respective surface of the intermediate element 11 in the roll-off direction can take place, which can be caused by a contact of the inner side walls of the seat of the connecting device (or the side walls of the seat delimiting the long holes laterally; see ref. number 30 of FIGS. 2 and 3, in the upper implant part correspondingly rotated by 90°) with the connecting device 4 at a pivoting or roll-off motion of the abutment part relative to the intermediate element. The slipping motion can preferably follow after the roll-off motion so that these two motions take place one after the other and not in manner superposed to one another. According to the preferred embodiment, the width of the long hole and the joint surface of the joint part are designed in such a manner that first a roll-off and then a slipping motion takes place, which may apply for both joint parts. Even in the "slipping motion", the joint part makes linear (not flat) contact with the respective abutment surface of the intermediate element.

According to the preferred embodiment, the connecting device 4 has a two-part configuration with two joinable parts such as a bolt 4a and a receiving pin or receiving sleeve 4b. The connecting element is axially secured relative to the intermediate element without play and preferably also against twisting, to which end the parts 4a, 4b in the fixed state each overlap and abut without play against the upper and lower side 12, 13 of the intermediate element 11 with annular abutment areas 4c, 4d thereof. The bolt 4a and the receiving sleeve 4b are permanently connected (preferably they cannot be detached from each other in a non-destructive manner) e.g. by laser welding on the frontal connecting area 4e (see FIG. 2) for example. The connection can be made with the abutment part in a completely or at least partially demounted state (preferably with both abutment parts not yet mounted), and the connection can be made at least substantially from the longitudinal direction of the connecting device or the longitudinal axis of the implant. That connection provides a coherent sub-assembly comprised of the joint parts, the intermediate element and the connecting element. The head-like enlarged connecting regions 24, 25 of the connecting device 4 are here arranged in seats 26, 27 of the two joint parts and overlap the holding areas of the joint parts for securing the two joint parts together with the intermediate element there between axially against one another.

The seat of at least one and in the embodiment the seats of both joint parts are provided with long holes 6b, 9b that enable a lateral displacement of the two implant parts 2, 3 transversely to the longitudinal axis of the connecting device relative to the connecting element. The long holes here extend in the longitudinal direction of the areas 18, 19 (presently designed as roll-off areas) that afford the articulated motion, hence the back of the joint parts, namely on the level of the back line (line of the highest elevation). The back line of the respective joint part runs in the center line of the respective long hole. The joint part of the upper and lower implant parts is thus designed as a sliding plate that is slidingly moved on the intermediate element by being displaced along the respective long hole. Accordingly, that sliding motion or displacement does not act in the direction of a demounting motion of a pair of joint and abutment parts.

Figure 3C:
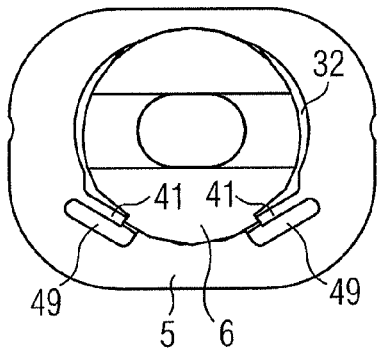
FIG. 3c is a top view thereof in a locked state.

The abutment parts 5, 8 are each detachably connected to the associated joint parts 6, 9, in the present case by respective form-closure devices, particularly by locking devices as shown in FIG. 3 for the paired abutment and joint parts (this correspondingly applies for the implant part 3). Concerning the form-closure devices, the other pair of these two parts is identically constructed. According to a preferred embodiment of the present invention, the fixing devices of the joint part and abutment part of the respective implant part can be operatively engaged with each other by twisting the two parts relative to each other, namely by twisting about the longitudinal axis 1*a* of the implant or the longitudinal axes 6*a*, 9*a* of the implant parts. Thus, as already noted, during an articulated motion of the implant, the form-closure devices are mostly located outside of the main lines of flux with respect to a motion in the direction of a detachment of the same, particularly outside of those lines of flux which run in the main plain of the implant so as to counteract any unintentional detachment of the form-closure devices. The fixing devices are designed in such a manner that the joint part and the abutment part must be joined in the direction of the longitudinal axis 1*a* of the implant in order to engage both parts in a first engagement position or joining position (see FIG. 3) and to move the parts from that position to their fixing position (see FIG. 3*c*) by a twisting motion. The abutment part and the joint part are thus positively locked in the axial direction of the longitudinal axis of the implant by holding areas 36 on the joint part. This makes joining easy. Accordingly, also the twisting motion for the fixing by means of the locking devices is performed about the joining direction (arrow F) that extends parallel to the longitudinal axes 6*a*, 9*a*.

The fixing device each preferably include a male and a co-acting female form-closure device, wherein the male form-closure device comprises a pin 35 or a base, which in the present case includes two radially projecting holding areas 36, and the female form-closure device comprises a non-round seat 37 including at least one undercut, the seat 37 serving to receive the abutment part for the joint element and including lateral convexities 32 for the insertion of the holding areas 36. The entire seat 37 thus has a non-round design. This simplifies the joining operation and enables the absorption of high forces so that the implant has a long service life. The holding devices 36 on the one side and the convexities 32 on the other side are mutually congruent in shape (in a top view thereof). The fixing area of the abutment part for the joint part thus includes a seat 37 in which the joint part can be inserted from its surface facing the abutment part in the mounted state of the implant, which makes the mounting of the implant easier. The form-closure devices can be joined to each other in a joining position and can be moved to their fixing position by being twisted. The form-closure devices are designed in such a manner that they can be moved from the engagement position/joining position to the fixing position on twisting without an axial displacement of the form-closure device to each other. The active surfaces of the form-closure devices do thus have no pitch. For that reason, the construction height of the implant can be particularly small and the forces acting on the implant parts during an articulated motion of the implant are well predictable and controllable. According to a preferred embodiment, the male form-closure device includes two or more radially projecting areas (holding areas 36) and the female closure device includes corresponding recesses 38 that permit the form-closure devices to be joined to each other and thus provide a stable, tilt and cant resistant design. To this end, the two radially projecting areas of the male form-closure device according to the embodiment are spaced from each other by 90° in the circumferential direction of the fixing device, in the present case by 180°. The two convexities are opposed to each other in the same manner as the two holding devices.

In a twisted position, the cooperating form-closure devices are secured against relative twisting by anti-twist safeguarding devices 40 (see FIG. 3) thus preventing the implant from unintentional demounting. The anti-twist safeguarding devices 40 include locking means 41 that reliably counteract unintentional demounting and afford high holding forces while being adjustable in position by means of an adjustment wrench 75 (FIG. 4*f*), e.g. from the locking position to the unlocking position, by turning the adjustment wrench. The tongue-like locking means 41 can engage in corresponding locking recesses 42 of the joint part in a manner which provides safety against twisting by locking in opposite directions. In this way, the implant is particularly well adapted for being remounted if necessary with the abutment and joint parts in a different combination. In the present case, two anti-twist safeguarding devices 40 are provided on the implant part, which lock the implant part and the abutment part against twisting in mutually opposite twisting directions. Thus safety against twisting is given in both directions while the holding force is maximal in each of the two directions.

The anti-twist safeguarding devices 40 which prevent twisting in opposite twisting directions are formed in such a manner that the respective anti-twist device simultaneously acts as a limit stop for the rotary motion of the joint part. When the joint part contacts an anti-twist safeguarding device that forms a limit stop in the respective direction of rotation, the anti-twist safeguarding device that is effective in the opposite direction of rotation, engages in its associated holding area, e.g. a locking recess 42, and secures the joint part against twisting in that other direction so that the joint part is finally secured against twisting relative to the abutment part in both directions of rotation. This can generally apply within in the scope of the present invention.

The fixing devices (e.g. pin and retainer) each have a longitudinal axis 39*a*, 39*b* (parallel to the axes 6*a*, 9*a*), and on the joint and/or abutment part areas with a larger or smaller radial distance from the longitudinal axis are provided. The anti-twist safeguarding devices are thus arranged in those regions 44 on the joint part which have the larger radial distance from the longitudinal axis, whereby the anti-twist safeguarding device can absorb higher forces and can be adjusted more accurately with regard to the prevention of smaller twisting motions.

The male and female form-closure devices comprise holding areas 36 which in the fixing position of the form-closure devices secure the joint and abutment parts 6, 9 in a play-free manner against mutual lateral tilting, whereby the stability of the implant at complex motions of the patients is increased.

On the joint part 6 and/or on the abutment part 9 of an implant part, in the region of the anti-twist safeguarding devices, an engagement opening 49 for the adjustment wrench 75 is provided which is accessible from outside (FIG. 1, 3). By engaging the adjustment wrench at the anti-twist safeguarding element, the latter can be moved to its locking position. The engagement opening simultaneously serves to permit an excursion of the locking device radially outwardly before locking in place.

The abutment part or the joint part include on the continuous lateral surface thereof through-holes 51 that communicate with the seat for the respective other one of the two parts and particularly with the region thereof in which the fixing devices for the joint part are arranged so that the anti-twist safeguarding devices can be unlocked by inserting a tool, e.g. a mandrel, or the adjustment wrench 75 in the through-holes, in order to allow the parts that are locked by means of the anti-twist safeguarding devices to be twisted and the implant to be demounted.

To make the mounting of the implant easier, one or both joint parts of the implant have lateral engagement surfaces 53 for the engagement of a torque tool 76. The engagement surfaces are adapted to the tool for torque transmission in order to turn the joint part about its longitudinal axis by means of the tool.

Further, a mounting plate 80 for mounting an implant according to the generic part of claim 1 and preferably for mounting an implant according to the present invention is provided. The mounting plate 81 includes at least one recess 81 for receiving an abutment part and/or a joint part. The recess is adapted to the contour of the associated abutment part or joint part in such a manner that the respective abutment part or joint part is received by the recess of the mounting plate so as to be secured against displacement with respect to the main plane of the mounting plate and against twisting with respect to the main axis of the abutment part or joint part. This considerably simplifies mounting because the respective part is positioned on the mounting plate during mounting, i.e. can be mounted while it is arranged in the recess. Accordingly, the mounting plate serves to fix the respective part during mounting. To this end, an insert 85 can be provided in addition, which is arranged in a seat and is preferably accurately adapted to the contour of the circumference and/or to the surface texture of the implant part to be arranged in the seat.

The mounting plate 80 can include at least two seats 81, 82 for receiving both abutment parts of the implant. The mounting plate can include at least or precisely four seats 81-85 for receiving both abutment parts 5, 8 and both joint parts 6, 9 of the implant. According to an alternative embodiment, the mounting plate can include at least or precisely five or six seats for receiving both abutment parts, both joint parts and the intermediate element 11 or the connecting element 4 or for receiving the intermediate element 11 and the connecting element 4. According to a further alternative embodiment, the mounting plate 80 can include at least or precisely five or six seats for receiving both abutment parts, both joint parts, the intermediate element and a two-part connecting element. In this way, the most important or all the component parts of the implant can be arranged and supported at a time on the mounting plate, for instance for checking the component parts before the implant is mounted. The seat can be respectively provided in the form of a recess in the mounting plate or in the form of a fixing protrusion or in any other suitable form that preferably permits the parts to be positioned on the mounting plate in a manner secure against displacement. It will be understood that the seats of the mounting plate are each adapted to the component parts to be received, particularly to the abutment and/or joint part, where necessary with the arrangement of a respective insert 85, so that the component parts are each arranged and preferably precisely fitted in the seat so as to be secured against displacement. The mounting kit which includes the mounting plate 80 can also comprise an adjustment wrench 75 that can be used for moving at least one of the anti-twist safeguarding devices to the anti-twist safeguarding position on the joint part.

For mounting (see FIG. 4*a-f*), an abutment plate, namely the cranial (as illustrated) or the caudal abutment plate, can be non-twistingly positioned on the seat of the mounting plate, with the fixing area for the corresponding joint part being upwardly directed. Both joint parts and the intermediate part are pre-mounted (see FIG. 2) by means of the connecting element, in order to form an assembly 87 ready for implantation. The corresponding joint part is inserted with its fixing area in the seat of the abutment part and is turned relative to the abutment part using the tool until the abutment part becomes locked. The fixing area of the second joint part then freely protrudes upwardly. Thereafter, the second abutment part is fixed in order to complete the implant. The pre-mounted assembly thus formed is preferably removed from the mounting plate and the fixing area of the second joint part is inserted in the seat of the abutment part that is positioned in its associated seat within the mounting plate. Thereafter, the second joint part is twisted relative to the second abutment part using the tool and is also locked against the abutment part. If necessary, also the second abutment part can be attached to the pre-mounted assembly and the joint part twisted relative to the abutment part, although this is more cumbersome and error-prone. Once the respective joint part is in its fixing position on the corresponding abutment part, the anti-twist safeguarding devices can be checked for and secured in their correct positioning by means of the adjustment wrench inserted in the engagement opening.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A joint implant comprising:
   a longitudinal axis;
   an upper implant part;
   a lower implant part articulated to the upper implant part to form a joint, each of the upper and lower implant parts having a joint part and an abutment part that can be abutted on and supported against respectively facing bone, the joint part and the abutment part of each respective implant part being detachably connected to each other by respective fixing devices, each abutment part having a fixing area including a seat into which the corresponding joint part is insertable in a direction parallel to the longitudinal axis from a surface facing the abutment part in a mounted state of the implant, the joint part and the abutment part of each of the upper and lower implant parts including a joint region, the two joint regions cooperating with each other directly to form an articulated connection, or with an intermediate element having opposite upper and lower sides as contact surfaces, thus forming two sub-joints; and
   a connecting device interconnecting the upper and lower implant parts to form a coherent assembly, wherein the connecting device can change position relative to one or both of the joint parts of the upper and lower implant parts, and
   wherein each fixing device detachably connecting the abutment part and the corresponding joint part of a respective implant part comprises form-closure devices fixable to one another in a fixed position by twisting the joint part and the abutment part of the respective implant part relative to one another, and at least one of said fixing devices further includes two anti-twist safeguarding devices for securing the form-closure devices in the fixed position against untwisting in an opposite twisting direction, each of said anti-twist safeguarding devices having a recess in a radially outward surface of the joint part engaged with a protrusion radially inwardly extending from the corresponding abutment part, said engagement being disengageable in a direction perpendicular to the longitudinal axis by a tool.

2. The joint implant according to claim 1, wherein the respective form-closure devices of each fixing device can be joined to one another in a longitudinal direction of the implant by being moved to a joining position and can be positively fixed to one another in the joining position by being twisted against each other with reference to a joining direction.

3. The joint implant according to claim 1, wherein for fixing the respective abutment part and the corresponding joint part to one another of each of the upper and lower implant parts, the respective form-closure devices of each of the upper and lower implant parts each includes a male and a female form-closure device that cooperate for fixing, the male form-closure device comprising a pin with radially protruding holding areas and the female form-closure device comprising a non-round seat including at least one undercut, the form-closure devices can be joined to one another in a joining position and can be moved to a fixing position by being twisted relative to each other.

4. The joint implant according to claim 3, wherein the form-closure devices can be joined to one another in the joining position and can be moved to the fixing position by twisting the form-closure devices relative to each other without axial displacement to each other.

5. The joint implant according to claim 3, wherein the pin of the male form-closure device includes two or more radially protruding holding areas and the female form-closure device includes corresponding recesses enabling the form-closure devices to be joined.

6. The joint implant according to claim 5, wherein the at least two radially protruding portions of the male form-closure device are spaced-apart from each other by more than 90° in a circumferential direction of the fixing device.

7. The joint implant according to claim 1, wherein each fixing device defines a respective longitudinal axis thereof, and portions with a larger or smaller radial distance from the longitudinal axis of the respective fixing device are provided on at least one of the joint part or the abutment part and anti-twist safeguarding devices are arranged on a portion with a larger radial distance from the longitudinal axis of the respective fixing device.

8. The joint implant according to claims 1, wherein the fixing devices include male and female form-closure devices, the male and female form-closure devices including holding areas which in a fixing position of the form-closure devices secure the joint and abutment parts relative to each other without play against lateral tilting.

9. The joint implant according to claim 1, wherein each abutment part includes through-holes on a continuous lateral surface thereof which communicate with the seat for the corresponding joint part.

10. The joint implant according to claim 1, wherein a connecting device penetrates both joint parts and an intermediate element, and is supported against the respective joint part in such a manner that the connecting device is secured against a displacement in an axial direction which would cause the parts to separate.

11. The joint implant according to claim 1, further comprising an intermediate element between the upper and lower implant parts, wherein the joint part of the upper and lower implant parts is formed as a sliding plate that can slide on, and relative to, the intermediate element during an articulated motion of the mounted implant.

12. The joint implant according to claim 1, wherein an externally accessible engagement opening for an adjustment wrench is provided on the joint part or on the abutment part or on both the joint part and the abutment part in the region of the anti-twist safeguarding devices so that the anti-twist safeguarding devices can be moved to a safeguarding position by means of the adjustment wrench.

13. The joint implant according to claim 12, wherein at least one of the joint parts defines lateral engagement surfaces which are adapted to a shape of a torque transmitting tool in order to turn the joint part about the longitudinal axis by means of the torque transmitting tool.

14. The joint implant according to claim 1, wherein at least one of the joint parts defines lateral engagement surfaces which are adapted to a shape of a torque transmitting tool in order to turn the joint part about the longitudinal axis by means of the torque transmitting tool.

15. The joint implant according to claim 1, further comprising an intermediate element between the upper and lower implant parts, wherein in a mounted state of the implant, the upper and lower implant parts can be twisted about the longitudinal axis relative to each other, relative to the intermediate element or relative to both.

16. The joint implant according to claim 15, wherein in the mounted state of the implant, the upper and lower implant parts can be displaced relative to each other, relative to the intermediate element or relative to both, in a direction transverse to the longitudinal axis of the implant.

17. The joint implant according to claim 1, further comprising an intermediate element between the upper and lower implant parts, wherein in a mounted state of the implant, the upper and lower implant parts can be displaced relative to each other, relative to the intermediate element or relative to both, in a direction transverse to the longitudinal axis.

18. The joint implant according to claim 1, wherein the abutment part has a continuous closed surface turned toward associated bone when implanted.

19. A joint implant assembly comprising the joint implant of claim 1 and a mounting device for mounting the joint implant the mounting device comprising a mounting plate including at least one seat for receiving at least one of the abutment part or the joint part, the seat being adapted to a contour of a circumference of the associated abutment part or joint part in a manner such that the respective abutment part or joint part is received in the at least one seat of the mounting plate so as to be secured against displacement with respect to a main plane of the mounting plate and secured against twisting with respect to a main axis of the abutment part or the joint part.

20. The joint implant assembly according to claim 19, wherein the mounting plate includes:
   a. at least two seats for receiving both abutment parts of the joint implant; or
   b. at least four seats for receiving both abutment parts and both joint parts of the joint implant; or
   c. at least five or six seats for receiving both abutment parts, both joint parts and an intermediate element between the upper and lower implant parts or the connecting device or for receiving the intermediate element and the connecting device; or
   d. at least five or six seats for receiving both abutment parts, both joint parts, an intermediate element between the upper and lower implant parts and the connecting device, or
   e. a seat for receiving at least the abutment part, the joint part, an intermediate element between the upper and lower implant parts and the connecting device.

21. The joint implant assembly according to claim 19, wherein the mounting plate further includes an insert arrangeable in the one seat, the insert corresponding to at least one of the contour of the circumference or the surface texture of an implant part that is to be arranged and accurately fitted in the at least one seat.

22. The joint implant assembly of claim 19, further comprising an adjustment wrench for moving at least one anti-twist safeguarding device to an anti-twist safeguarding position on the joint part, or a torque wrench for fixing the joint part to the abutment part by turning.

23. A joint implant assembly comprising the joint implant of claim 2 and a mounting device for mounting the joint implant the mounting device comprising a mounting plate including at least one seat for receiving at least one of the abutment part or the joint part, the at least one seat being adapted to a contour of a circumference of the associated abutment part or joint part in a manner such that the respective abutment part or joint part is received in the at least one seat of the mounting plate so as to be secured against displacement with respect to a main plane of the mounting plate and secured against twisting with respect to a main axis of the abutment part or the joint part.

24. A joint implant comprising:
an upper implant part;
a lower implant part articulated to the upper implant part to form a joint, each of the upper and lower implant parts having a joint part and a corresponding abutment part that can be abutted on and supported against respectively facing bone, the corresponding joint and abutment parts of each respective implant part being detachably connected to each other by respective fixing devices, each abutment part having a fixing area including a fully circumferential seat into which the corresponding joint part is insertable from a surface facing the abutment part in a mounted state of the implant, and each abutment part including through-holes on a continuous lateral surface thereof for communicating with a seat for the corresponding joint part, the corresponding joint and abutment parts of each of the upper and lower implant parts including a joint region, the two joint regions cooperating with each other directly to form an articulated connection, or with an intermediate element having opposite upper and lower sides as contact surfaces, thus forming two sub-joints; and
a connecting device interconnecting the upper and lower implant parts to form a coherent assembly, wherein the connecting device can change position relative to one or both of the joint parts of the upper and lower implant parts,
wherein each fixing device detachably connecting the abutment part and the joint part of a respective implant part comprises form-closure devices fixable to one another in a fixed position by twisting the joint part and the abutment part of the respective implant part relative to one another, the form-closure devices having anti-twist safeguarding devices for securing the form-closure devices in a fixed position against further twisting, said anti-twist safeguarding devices including locking recesses of a respective joint part engaged at an inner surface thereof by locking tongues on the corresponding abutment part in a manner secured against twisting, wherein the through-holes of the abutment part are adapted to receive a tool for engaging the locking tongues and disconnecting the locking tongues from the locking recesses of the corresponding joint part.

* * * * *